United States Patent [19]

Lohri et al.

[11] Patent Number: 5,631,366

[45] Date of Patent: May 20, 1997

[54] PROCESS FOR MAKING 3-FORMYLCEPHEM DERIVATIVES

[75] Inventors: Bruno Lohri, Kaiseraugst; Peter Vogt, Münchenstein, both of Switzerland

[73] Assignee: Hoffmann-La Roche Inc., Nutley, N.J.

[21] Appl. No.: 573,825

[22] Filed: Dec. 18, 1995

[30] Foreign Application Priority Data

Jan. 12, 1995 [CH] Switzerland ................. 93/95

[51] Int. Cl.$^6$ ................................ C07D 501/26
[52] U.S. Cl. ............................. 540/215; 540/230
[58] Field of Search ........................ 540/215, 230

[56] References Cited

U.S. PATENT DOCUMENTS 3,984,401 10/1976 Terao et al. ............... 260/243

FOREIGN PATENT DOCUMENTS

| 445821 | 9/1991 | European Pat. Off. . |
| 2 128 605 | 6/1971 | Germany . |
| 1356437 | 6/1974 | United Kingdom . |

OTHER PUBLICATIONS

Inokuchi, et al., *J. Org. Chem.*, 55(2):462–466 (1990).
Anelli, Pier Lucio, et al., *J. Org. Chem.*, 52:2559–2562 (1987).
Anelli, Pier Lucio, et al., *Organic Syntheses*, Coll. 8:367–371 (1993).
Green, T., Protective Groups In Organic Synthesis, Chap. 5, John Wiley and Sons, Inc., pp. 152–192, 218–287 (1981).
Inokuchi, Tsutomu, *J. Org. Chem.*, 56:2416–2421 (1991).
Inokuchi, Tsutomu, *Chemistry Letters*, pp. 1411–1414 (1994).
Rozantsev, Eduard, G., et al., *Synthesis*, pp. 190–202 (1971).

*Primary Examiner*—John M. Ford
*Attorney, Agent, or Firm*—George W. Johnston; Dennis P. Tramaloni; Alan P. Kass

[57] ABSTRACT

The present invention is concerned with a novel process for the making of a compound of formula I

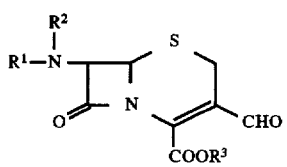

by oxidizing the corresponding 3-hydroxymethyl-cephem derivative with an inorganic hypohalite or inorganic halite in the presence of compounds of formula III

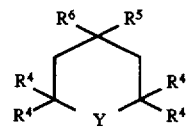

is wherein $R^1$, $R^2$, $R^3$, $R^4$, $R^5$, $R^6$, and Y are as defined herein.

The process is useful for providing 3-formyl-cephem compounds useful in the making of cephalosporin derivatives.

34 Claims, No Drawings

PROCESS FOR MAKING 3-FORMYLCEPHEM DERIVATIVES

BACKGROUND OF THE INVENTION

This invention relates to a novel process for the making of 3-formylcephem derivatives.

SUMMARY OF THE INVENTION

The present invention is concerned with a process for the making of a compound of formula I

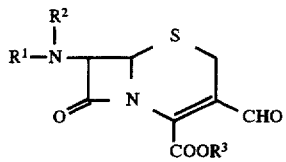

wherein $R^1$ is hydrogen or an amino protecting group;
$R^2$ is hydrogen or an amino protecting group; and
$R^3$ is a carboxylic acid protecting group;

comprising oxidizing the corresponding 3-hydroxymethyl-cephem derivative, and then recovering the compound of formula I.

The process in accordance with the invention comprises oxidizing a compound of formula II

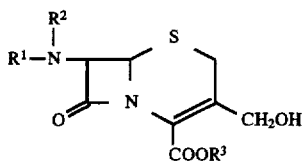

wherein $R^1$, $R^2$ and $R^3$ are as defined above, with an inorganic hypohalite or inorganic halite in the presence of a compound of formula III

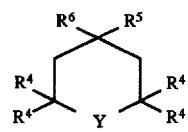

wherein $R^4$ is lower alkyl;

$R^5$ and $R^6$ either are both hydrogen or are both lower alkoxy or one of $R^5$ and R6 is hydrogen and the other of $R^5$ and $R^6$ is hydroxy, lower alkoxy, alkylcarbonyloxy, arylcarbonyloxy or NH—CO-lower-alkyl; or $R^5$ and $R^5$ taken together are a ketal group selected from a formula IVa–IVc

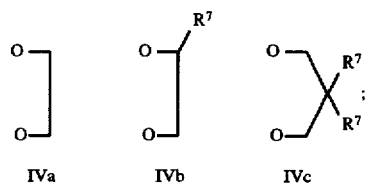

$R^7$ is lower alkyl;

Y is a group selected from a formula Va–Vc

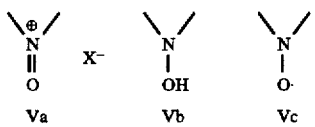

and $X^-$ is an anion, and thereafter recovering the compound of formula I.

The oxidation of the compound of formula II is also conveniently carried out with an inorganic hypohalite or halite in the presence of either a buffer and a compound of formula III or a buffer, a bromide ion source, and a compound of formula III.

DETAILED DESCRIPTION OF THE INVENTION

The present invention is concerned with a process for the making of a compound of formula I

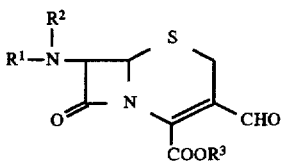

wherein $R^1$ is hydrogen or an amino protecting group;
$R^2$ is hydrogen or an amino protecting group; and
$R^3$ is a carboxylic acid protecting group;

comprising oxidizing the corresponding 3-hydroxymethyl-cephem derivative, and then recovering the compound of formula I.

A known process for the production of 3-formyl-cephem derivatives comprises oxidizing the corresponding 3-hydroxymethyl compounds with aliphatic sulphoxides in the presence of carboxylic anhydrides (DE 2128605). However, this process has certain disadvantages, since not only isomerization reactions of the double bond in the cephem ring but also lactone formations can occur. If dimethyl sulphoxide is used as the aliphatic sulphoxide, then the very unpleasant odor of the dimethyl sulphide reaction product is critical.

The present invention now provides a process for the making of 3-formyl-cephem derivatives which does not have the disadvantages of the process disclosed in DE 2128605.

The process in accordance with the invention comprises oxidizing a compound of formula II

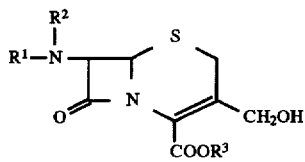

wherein $R^1$, $R^2$ and $R^3$ are as defined above, with an inorganic hypohalite or inorganic halite in the presence of a compound of formula III

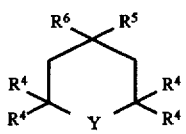

wherein

R$^4$ is lower alkyl;

R$^5$ and R$^6$ either are both hydrogen or are both lower alkoxy or one of R$^5$ and R$^6$ is hydrogen and the other of R$^5$ and R$^6$ is hydroxy, lower alkoxy, alkylcarbonyloxy, arylcarbonyloxy or NH—CO-lower-alkyl; or R$^5$ and R$^6$ taken together are a ketal group selected from a formula IVa–IVc

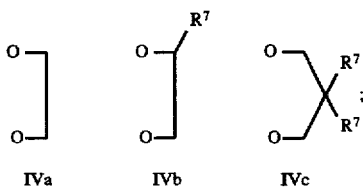

R$^7$ is lower alkyl;
Y is a group selected from a formula Va–Vc

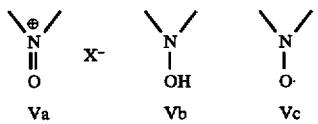

and X$^-$ is an anion,
and thereafter recovering the compound of formula I.

The oxidation of the compound of formula II is usually carried out with an inorganic hypohalite or halite in the presence of either a buffer and a compound of formula III or a buffer, a bromide ion source, and a compound of formula III.

It will be appreciated by those of ordinary skill in the art that each R$^4$ and R$^7$ moiety can be the same or different lower alkyl. For example, the R$^4$s at position 2 can be methyl and the R$^4$s at position 6 can be ethyl.

The oxidation of alcohols to aldehydes with sodium hypochlorite as the oxidizing agent and 4-methoxy-2,2,6,6-tetramethylpiperidine 1-oxide as the catalyst is in principle known (J. Org. Chem. vol. 52, No. 12, 1987, page 2559–2562). However, with respect to the reaction of unsaturated alcohols, the unsatisfactory selectivity and poor yields of this oxidation reaction caused by side reactions have been pointed out (Organic Syntheses, Coil. Vol. 8 1993 p. 369). It is therefore surprising that the oxidation of unsaturated alcohols of formula II in accordance with the invention proceeds with high selectivity and high yields.

The term "amino protecting group" includes protecting groups which are usually used to replace one proton or both protons of the amino group. Examples of such groups are described in Green T. Protective Groups in Organic Synthesis, Chapter 5, John Wiley and Sons, Inc. (1981), pp. 218–287, incorporated herein by reference. Known examples of such protecting groups are: benzylcarbonyl, benzyl-oxycarbonyl, tert.-butyloxycarbonyl, trimethylsilyl, trimethyl-silylethoxycarbonyl, trichloroethoxycarbonyl, o-nitrophenyl-sulphenyl, phthaloyl and the like. Tert.butyloxycarbonyl (BOC) and benzylcarbonyl are preferred protecting groups.

The term "carboxylic acid protecting group" includes protecting groups which are usually used to replace a proton of the carboxyl group. Examples of such groups are described in Green T. Protective Groups in Organic Synthesis, Chapter 5, John Wiley and Sons, Inc. (1981), pp. 152–192, incorporated herein by reference. Known examples of such protecting groups are: benzhydryl, tert butyl, p-nitrobenzyl, p-methoxybenzyl, methoxymethyl and the like. Benzhydryl is a preferred protecting group.

The term "lower alkyl" embraces straight-chain or branched saturated hydrocarbon residues with up to 7 carbon atoms such as methyl, ethyl, n-propyl, isopropyl, n-butyl, sec butyl, isobutyl, n-pentyl, n-hexyl and the like.

The term "alkyl" embraces straight-chain or branched saturated hydrocarbon residues with up to and including 14 carbon atoms such as octyl, decyl, dodecyl, tetradecyl, hexadecyl and the like.

The term "lower alkoxy" denotes lower alkyl groups in the sense of the foregoing definition which are attached via an oxygen atom, such as for example, methoxy, butyloxy and hexyloxy.

The term "alkylcarbonyloxy" denotes alkylcarbonyl residues attached via an oxygen atom. The term "alkylcarbonyl" denotes alkyl groups attached via a carbonyl group and embraces not only lower alkylcarbonyl groups such as acetyl or propionyl and the like but also longer alkylcarbonyl groups such as for example, caproyl (six carbon atoms), capryloyl (eight carbon atoms), capryl (ten carbon atoms), and the like.

The term "arylcarbonyloxy" denotes arylcarbonyl residues attached via an oxygen atom. The term "arylcarbonyl" denotes aryl groups attached via a carbonyl group. The term "aryl" denotes a sixmembered, aromatic, unsubstituted or substituted cyclic residue which is attached via a carbon atom, such as, for example, an unsubstituted or substituted phenyl residue, with lower alkyl groups or lower alkoxy groups coming into consideration, for example, as substituents.

In accordance with the invention a compound of formula II can be completely or partially dissolved in an organic solvent.

Suitable solvents in the scope of the present invention can be methylene chloride, ethyl acetate, chloroform, butyl acetate, diethyl ether, tert butyl methyl ether, dichloroethane and the like as well as mixtures of such solvents with one another or with tetrahydrofuran. Dichloromethane and ethyl acetate are preferred.

The oxidizing agents used include those selected from inorganic hypohalites and inorganic halites. Inorganic hypohalites include those such as for example, those selected from sodium hypochlorite, potassium hypochlorite, calcium hypochlorite, sodium hypobromite and the like. Inorganic halites include those such as for example, those selected from sodium bromite and potassium bromite (J. Org. Chemistry, Vol 56, 1991, page 2416–2421).

The oxidizing agent can be used in the form of aqueous solutions or can also be formed in situ by electrochemical reaction, for example, in the manner described in Chemistry Letters, 1994, page 1411–1414.

For the complete oxidation of the compound of formula II, a 3-hydroxymethyl-cephem derivative, to the compound of formula I, a 3-formyl-cephem derivative, at least equimolar amounts of the hypochlorite based on the amount of the compound of formula II, a 3-hydroxymethyl-cephem derivative, are required for example, when a hypochlorite is used as the oxidizing agent, but it is preferable to use the hypochlorite in an excess of up to 100%, that is, about 1 to 2 mol equivalents.

The oxidation is carried out in the presence of compounds of formula III as a catalyst. The addition of a catalyst is essential for the oxidation in accordance with the invention. Preferably, $R^4$ is methyl and Y is formula Va. Also preferred is $R^5$ and $R^6$ are both hydrogen or one of $R^5$ and $R^6$ is hydrogen and the other of $R^5$ and $R^6$ is lower alkoxy, alkylcarbonyloxy, or NH—CO-lower-alkyl; or $R^5$ and $R^6$ taken together are a group selected from

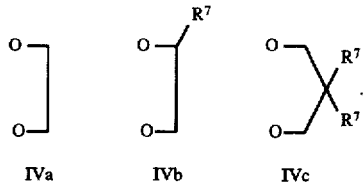

It is also preferred that either $R^5$ and $R^6$ are both hydrogen or one of $R^5$ and $R^6$ is hydrogen and the other of $R^5$ and $R^6$ is lower alkoxy. 2,2,6,6-Tetramethyl compounds of formula III are preferred catalysts. The 2,2,6,6-tetramethylpiperidin-1-oxyl radical (TEMPO) is especially preferred.

The preparation of the compounds of formula III is described, for example, in Synthesis, 1971, p. 190 et seq.

The oxidation of 3-hydroxymethyl-cephem derivatives of formula II is effected using from about 1 to about 20 mole %, preferably from about 3 to about 7 mole % of compound of formula III based on the starting material.

A buffer, such as selected from for example, sodium hydrogen carbonate, sodium acetate, disodium hydrogen phosphate and the like and combinations thereof, are normally used together with the oxidizing agent to carry out the oxidation.

The oxidation is promoted by adding a source of bromide ions which are conveniently introduced in the form of sodium or potassium bromide in amounts of from about 1 to about 20 mol % with respect to the 3-hydroxymethyl-cephem derivative, compound of formula II, unless a bromine-containing oxidizing agent is used, in which case the addition of bromide is superfluous.

The oxidation is conveniently effected in a temperature range of from about −15° C. to about 50° C., preferably at a temperature range of from about 0° C. to about 5° C. Conveniently, it can be performed under atmospheric pressure.

Conveniently, all reactants with the exception of the oxidizing agent are provided and the oxidizing agent is added in measured quantities.

The working up of the crude product to 3-formyl-cephem derivatives can be effected by extraction with solvents such as methylene chloride, ethyl acetate, tert.butyl methyl ether and the like. Further purification can be effected by recrystallization or reprecipitation.

By means of the process in accordance with the invention conversions of 3-hydroxymethyl-cephem derivatives into 3-formyl-cephem derivatives with high, frequently almost quantitative, yields can be achieved.

These 3-formyl-cephem derivatives are valuable intermediates in the synthesis of cephalosporin derivatives. For example, cephalosporin derivatives of formula VI

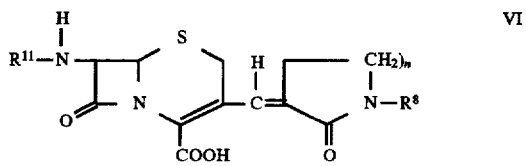

wherein $R^{11}$ is an acyl group derived from a carboxylic acid, $R^8$ is hydrogen, hydroxy, lower alkyl-qm, cycloalkyl, lower alkoxy, lower alkenyl, cycloalkenyl, lower alkynyl, aralkyl-$Q_m$, aryl-$Qr_m$, aryloxy, aralkoxy or a heterocyclic ring;

Qm is —CO— or —$SO_2$;

m is 0 or 1; and n is 0, 1 or 2, can be made as described in EP-A-0 620 225.

The following Examples illustrate the invention in more detail, but are not intended to be a limitation in any manner.

EXAMPLE 1

Synthesis of (6R,7R)-7-[(1,1-dimethylethoxy) carbonylamino]-3-formyl8-oxo-5-thia-1-aza-bicyclo [4.2.0.]oct-2-ene-2-carboxylic acid-benzhydryl ester using dichloromethane as the solvent.

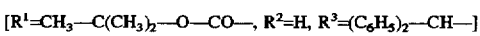

[$R^1$=$CH_3$—C($CH_3$)$_2$—O—CO—, $R^2$=H, $R^3$=($C_6H_5$)$_2$—CH—]

3.0 g (6 mmol) of (6R,7R)-7-[(1,1-dimethylethoxy)-carbonylamino]-3-hydroxymethyl-8-oxo-5-thia-1-aza-bicyclo-[4.2.0.]oct-2-eneo-2-carboxylic acid benzhydryl ester were dissolved in 24 ml of dichloromethane while warming to 35° C. After cooling the solution to 22° C. a solution of 90 mg (0.76 mmol) of potassium bromide and 240 mg (2.86 mmol) of sodium bicarbonate in 24 ml of water were added. The solution was cooled to 0° C. while stirring continuously (about 600 rpm) and then treated with 60 mg (0.38 mmol) of 2,2,6,6-tetramethylpiperidin-1-oxyl radical (TEMPO). 3.6 ml (7.2 mmol) of 15 percent (w/v) aqueous sodium hypochlorite solution were dosed in at 0°–2° C. within 1 hr. Stirring of the reaction mixture was continued for a further 30 min., then the reaction had finished according to thin-layer analysis. Working up of the reaction mixture was effected in the usual manner by extraction with dichloromethane/water and washing the organic phases with dil. sodium chloride solution. Drying and evaporation of the oganic phases gave 3.2 g of crude product with a 94.4% (HPLC area percent) content of (6R,7R)-7-[(1,1-dimethylethoxy) carbonylamino]-3-formyl-8-oxo-5-thia-1-aza-bicyclo[4.2.0.]oct-2-ene-2-carboxylic acid benzhydryl ester. Recrystallization of the crude product gave 2.49 g (83% of theory) of white crystals, m.p. 172°–173° C., with a 99.0% (HPLC area percent) content of (6R,7R)-7-[(1,1-dimethylethoxy)-carbonylamino]-3-formyl-8-oxo-5-thia-1-aza-bicyclo[4.2.0.]oct-2-ene-2-carboxylic acid benzhydryl ester.

EXAMPLE 2

Synthesis of (6R,7R)-7-[(1,1-dimethylethoxy) carbonylamino]-3-formyl-8-oxo-5-thia-1-aza-bicyclo [4.2.0.]oct-2-ene-2-carboxylic acid benzhydryl ester using ethyl acetate as the solvent.

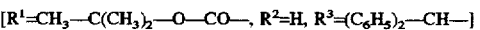

[$R^1$=$CH_3$—C($CH_3$)$_2$—O—CO—, $R^2$=H, $R^3$=($C_6H_5$)$_2$—CH—]

9.0 g (18 mmol) of (6R,7R)-7-[(1,1-dimethylethoxy)-carbonylamino]-3-hydroxymethyl-8-oxo-5-thia-1-azabicyclo[4.2.0.]oct-2-ene-2-carboxylic acid benzhydryl ester were partially dissolved in 74 ml of ethyl acetate. A solution of 270 mg (2.:3 mmol) of potassium bromide and 720 mg (8.6 mmol) of sodium bicarbonate in 66 ml of water were added. The mixture was cooled to 0° C. while stirring continuously and then treated with a solution of 180 mg (1.15 mmol) of 2,2,6,6-tetramethylpiperidin-1-oxyl radical (TEMPO) in 1 ml of ethyl acetate. 9.15 ml (21.8 mmol) of 17.7 percent (w/v) aqueous sodium hypochlorite solution were dosed in at 0°–2° C. within 1 hr. Stirring of the reaction mixture was continued for a further 15 min., then the reaction had finished according to thin-layer analysis. The working up of the reaction mixture was effected in the usual manner by extraction with ethyl acetate/water and washing the organic phases with dil. sodium chloride solution. Drying and evaporation of the organic phases and recrystallization of the crude product gave 8.1 g (91% of theory) of white crystals with a 96.4% (HPLC area percent) content of (6R,7R)-7-[(1,1-dimethylethoxy)carbonylamino]-3-formyl-8-oxo-5-thia-1-aza-bicyclo[4.2.0.]oct-2-ene-2-carboxylic acid benzhydryl ester.

EXAMPLE 3

Synthesis of (6R,7R)-7-benzylcarbonylamino-3-formyl-8-oxo-5-thia-1-aza-bicyclo[4.2.0.]oct-2-ene-2-carboxylic acid benzhydryl ester using a mixture of dichloromethane and tetrahydrofuran (THF) as the solvent.

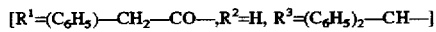

$[R^1=(C_6H_5)-CH_2-CO-, R^2=H, R^3=(C_6H_5)_2-CH-]$ 9.3 g (18 mmol) of (6R,7R)-7-benzylcarbonylamino-3-hydroxym ethyl-8-oxo-5-thia-1-aza-bicyclo [4.2.0. ]oct-2-ene-2-carboxylic acid benzhydryl ester were partially dissolved in a mixture of 24 ml of dichloromethane and 12 ml of THF. A solution of 270 mg (2.3 mmol) of potassium bromide and 720 mg (8.6 mmol) of sodium bicarbonate in 66 ml of water were added. The mixture was cooled to 0° C. while stirring continuously and then treated with 105 mg (0.67 mmol) of 2,2,6,6-tetramethylpiperidin-1-oxyl radical (TEMPO). 9 ml (21.6 mmol) of 17.9 percent (w/v) aqueous sodium hypochlorite solution were dosed in at 0°–2° C. within 1 hr. Stirring of the reaction mixture was continued for a further 15 min., then the reaction had finished according to thin-layer analysis. The working up of the reaction mixture was effected in the usual manner by extraction with dichloromethane/water. Drying and evaporation of the organic phases and re-precipitation of the crude product gave 8.9 g (96% of theory) of white powder, m.p. 130°–132° C., with a content of 98.7% (HPLC area percent) of (6R, 7R)-7-benzylcarbonylamino-3-formyl-8-oxo-5-thia-1-aza-bicyclo-[4.2.0.]oct-2-ene-2-carboxylic acid benzhydryl ester.

EXAMPLE 4–12

Oxidation of (6R,7R)-7-[(1,1-dimethylethoxy) carbonylamino]-3-hydroxymethyl-8-oxo-5-thia-1-aza-bicyclo[4.2.0. ]oct-2-ene-2-carboxylic acid benzhydryl ester in the presence of additional catalysts of formula III.

(6R,7R)-7-[(1,1-Dimethylethoxy)carbonylamino]-3-hydroxymethyl-8-oxo-5-thia-1-aza-bicyclo[4.2.0.]oct-2-ene-2-carboxylic acid benzhydryl ester (batch sizes of 0.5 g to 3 g) were converted in the manner described in Example 1 with 1.2 mol equivalents of sodium hypochlorite solution into the corresponding 3-formylcephem derivative, (6R,7R) -7-[(1,1-dimethylethoxy) carbonylamino]-3-formyl-8-oxo-5-thia-1-aza-bicyclo[4.2.0.]oct-2-ene-2-carboxylic acid benzhydryl ester. In contrast to Example 1 there were used in place of TEMPO additional catalysts of formula III in an amount of 6.4 mol percent with respect to the starting material unless indicated otherwise.

The catalysts used and the yields of 3-formylcephem derivative obtained are compiled in Tables 1 and 2.

TABLE 1

| | Catalyst<br>$R^4 = CH_3$, $R^5 = H$<br>Y = formula Vc | % 3-Formyl-cephem derivative<br>(area percent HPLC) |
|---|---|---|
| Example 4 | $R^6 = OCH_3$ | 90.4 |
| Example 5 | $R^6 = O(CH_2)_5-CH_3$ | 87.7 |
| Example 6 | $R^6 = O(CH_2)_3-CH_3$ | 87.1 |
| Example 7 | $R^6 = NH-COCH_3$[1) | 82.8 |
| Example 8 | $R^6 = OCO(CH_2)_4-CH_3$ | 81.0 |
| Example 9 | $R^6 = OCOCH(CH_3)_2$ | 78.9 |

[1)]4.7 mol percent

TABLE 2

| | Catalyst<br>$R^4 = CH_3$;<br>Y = formula Vc | % 3-Formyl-cephem derivative<br>(area percent HPLC) |
|---|---|---|
| Example 10 | 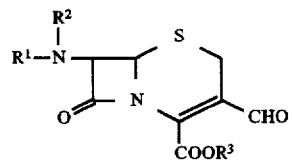 $R^5, R^6 =$ | 93.9 |
| Example 11 | $R^5, R^6 =$ (structure) | 91.7 |
| Example 12 | 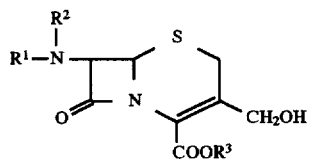 $R^5, R^6 =$ | 89.8 |

What is claimed is:
1. A process for making a compound of formula I

$$\begin{array}{c} R^2 \\ | \\ R^1-N \\ \\ O \end{array} \begin{array}{c} S \\ \\ N \\ \\ COOR^3 \end{array} CHO \qquad I$$

wherein $R^1$ is hydrogen or an amino protecting group;

$R^2$ is hydrogen or an amino protecting group; and $R^3$ is a carboxylic acid protecting group;

comprising oxidizing a compound of formula II $$\begin{array}{c} R^2 \\ | \\ R^1-N \\ \\ O \end{array} \begin{array}{c} S \\ \\ N \\ \\ COOR^3 \end{array} CH_2OH \qquad II$$

wherein $R^1$, $R^2$ and $R^3$ are defined as above, with an inorganic hypohalite or inorganic halite in the presence of a compound of formula III

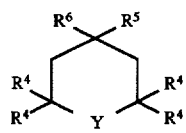

wherein $R^4$ is lower alkyl;

$R^5$ and $R^6$ either are both hydrogen or are both lower alkoxy or one of $R^5$ and $R^6$ is hydrogen and the other of $R^5$ and $R^6$ is hydroxy, lower alkoxy, alkylcarbonyloxy, arylcarbonyloxy or NH—CO-lower-alkyl; or $R^5$ and $R^6$ taken together are a ketal group selected from a formula IVa–IVc

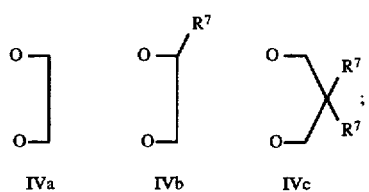

$R^7$ is lower alkyl;
Y is a group selected from a formula Va–Vc

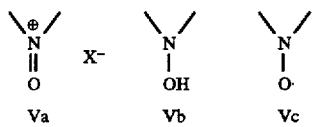

and $X^-$ is an anion,
and thereafter recovering the compound of formula I.

2. The process according to claim 1 wherein $R^4$ is methyl.
3. The process according to claim 2 wherein Y is formula

4. The process according to claim 3 wherein $R^5$ and $R^6$ are both hydrogen or one of $R^5$ and $R^6$ is hydrogen and the other of $R^5$ and $R^6$ is lower alkoxy, alkylcarbonyloxy, or NH—CO-lower-alkyl; or $R^5$ and $R^6$ taken together are a group selected from

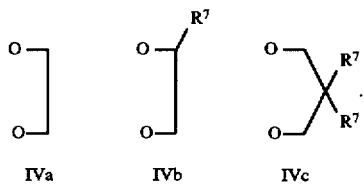

5. The process according to claim 4 wherein $R^5$ and $R^6$ are both hydrogen.
6. The process according to claim 5 wherein the compound of formula III is 2,2,6,6-tetramethylpiperidine 1-oxide.
7. The process according to claim 4 wherein one of $R^5$ and $R^6$ is hydrogen and the other of $R^5$ and $R^6$ is lower alkoxy, alkylcarbonyloxy, or NH—CO-lower-alkyl.
8. The process according to claim 7 wherein one of $R^5$ and $R^6$ is hydrogen and the other of $R^5$ and $R^6$ is lower alkoxy.

9. The process according to claim 8 wherein the compound of formula III is selected from the group of 4-methoxy-2,2,6,6-tetramethylpiperidine 1-oxide, 4-butoxy-2,2,6,6-tetramethylpiperidine 1-oxide, or 4-hexyloxy-2,2,6,6-tetramethylpiperidine 1-oxide.
10. The process according to claim 9 wherein the compound of formula III is 4-methoxy-2,2,6,6-tetramethylpiperidine 1-oxide.
11. The process according to claim 4 wherein one of $R^5$ and $R^6$ is hydrogen and the other of $R^5$ and $R^6$ is alkylcarbonyloxy.
12. The process according to claim 4 wherein $R^5$ and $R^6$ taken together are a group selected from

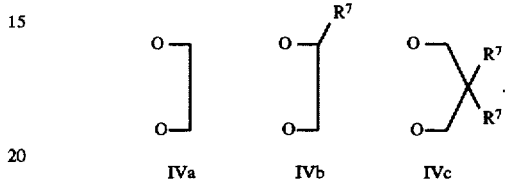

13. The process according to claim 12 wherein $R^5$ and $R^6$ taken together are

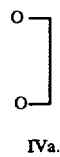

14. The process according to claim 12 wherein $R^5$ and $R^6$ taken together are

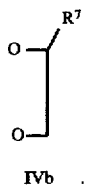

15. The process according to claim 14 wherein $R^7$ is ethyl.
16. The process according to claim 12 wherein $R^5$ and $R^6$ taken together are

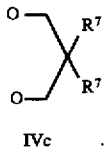

17. The process according to claim 16 wherein $R^7$ is methyl.
18. The process according to claim 1 wherein the compound of formula III is present in an amount of from about 1 to about 20 mol % based on the starting material of formula II.
19. The process according to claim 18 wherein the compound of formula II! is present in an amount of from about 3 to about 7 mol %.
20. The process according to claim 19 wherein the compound of formula III is selected from 2,2,6,6-tetramethylpiperidine 1-oxide and 4-methoxy-2,2,6,6-tetramethylpiperidine 1-oxide.

21. The process according to claim 1, wherein the amount of the inorganic hypohalite or inorganic halite is present in amount of about 1 to 2 mol equivalents based on the amount of the compound of fornula II.

22. The process according to claim 21, wherein the inorganic hypohalite is selected from sodium hypochlorite, potassium hypochlorite, calcium hypochlorite, and sodium hypobromite.

23. The process according to claim 22 wherein the inorganic hypohalite is sodium hypochlorite.

24. The process according to claim 21 wherein the inorganic halite is selected from sodium bromite and potassium bromite.

25. The process according to claim 1 wherein the buffer is selected from sodium hydrogen carbonate, sodium acetate, disodium hydrogen phosphate, and combinations thereof.

26. The process according to claim 25 wherein a bromide ion source is added.

27. The process according to claim 26 wherein the bromide ion source is selected from of sodium bromide and potassium bromide.

28. The process according to claim 27 wherein the bromide ion source is potassium bromide.

29. The process according to claim 27 wherein the buffer is sodium hydrogen carbonate and the bromide ion source is potassium bromide.

30. The process according to claim 1 wherein the compound of formula II is completely or partially dissolved in an organic solvent.

31. The process according to claim 30 wherein the organic solvent is selected from methylene chloride, ethyl acetate, chloroform, butyl acetate, diethyl ether, tert butyl methyl ether, dichloroethane, mixtures of said solvents, and mixtures of said solvent with tetrahydrofuran.

32. The process according to claim 31 wherein the organic solvent is selected from ethyl acetate and dichloroethane.

33. The process according to claim 1 wherein the oxidation is carried out at in a temperature range of from about −15° C. to about 50° C.

34. The process according to claim 33 wherein the oxidation is carried out at in a temperature range of from about 0° C. to about 5° C.

* * * * *

UNITED STATES PATENT AND TRADEMARK OFFICE
CERTIFICATE OF CORRECTION

PATENT NO. : 5,631,366
DATED : May 20, 1997
INVENTOR(S) : Bruno Lohri and Peter Vogt It is certified that error appears in the above-indentified patent and that said Letters Patent is hereby corrected as shown below:

In claim 19, column 10, line 62, delete "II!" and insert therefor -- III --.

In claim 20, column 10, line 65, delete "II1" and insert therefor -- III --.

In claim 21, column 11, line 4, delete "fornula" and insert therefor -- formula --.

*In claim 27, column 11, line 21, delete "of" between "from" and "sodium".

In claim 31, column 12, line 11, delete "tert butyl" and insert therefor -- tert.butyl --.

In claim 33, column 12, line 18, delete "-15° C." and insert therefor -- -15° C --.

In claim 34, column 12, line 21, delete "0° C." and insert therefor -- 0° C --.

Signed and Sealed this

Nineteenth Day of August, 1997

*Attest:*

BRUCE LEHMAN

*Attesting Officer*     Commissioner of Patents and Trademarks